(12) United States Patent
Grabis et al.

(10) Patent No.: US 6,736,794 B2
(45) Date of Patent: *May 18, 2004

(54) METHOD AND DEVICE TO PROTECT SYRINGES AND SIMILAR MEDICAL INSTRUMENTS

(75) Inventors: Dietrich W. Grabis, San Rafael, CA (US); Mary Anne Kaehler, Lodi, CA (US); Kenneth Mellberg, Stateline, NV (US)

(73) Assignee: ITG-International Technology Group, LLC, San Rafael, CA (US)

( * ) Notice: Subject to any disclaimer, the term of this patent is extended or adjusted under 35 U.S.C. 154(b) by 193 days.

This patent is subject to a terminal disclaimer.

(21) Appl. No.: 09/995,960

(22) Filed: Nov. 27, 2001

(65) Prior Publication Data

US 2002/0087124 A1 Jul. 4, 2002

Related U.S. Application Data

(63) Continuation-in-part of application No. 09/524,144, filed on Mar. 10, 2000, now Pat. No. 6,322,540, and a continuation-in-part of application No. PCT/US01/07646, filed on Mar. 9, 2000.

(51) Int. Cl.[7] .................................................. A61M 5/00
(52) U.S. Cl. ...................... 604/110; 604/195; 604/198; 604/220; 604/263
(58) Field of Search ................................. 604/110, 198, 604/263, 192, 195, 218, 220, 221, 228

(56) References Cited

U.S. PATENT DOCUMENTS

| | | |
|---|---|---|
| 3,880,163 A | 4/1975 | Rikkerskamp |
| 5,147,303 A | 9/1992 | Martin |
| 5,279,582 A | 1/1994 | Davison et al. |
| 5,411,487 A | 5/1995 | Castagna |
| 5,527,294 A | 6/1996 | Weatherford et al. |
| 5,591,138 A | 1/1997 | Vaillancourt |
| 5,885,257 A | 3/1999 | Badger |

*Primary Examiner*—Brian L. Casler
*Assistant Examiner*—Jeremy Thissell
(74) *Attorney, Agent, or Firm*—Dorsey & Whitney LLP

(57) ABSTRACT

A needle-stick safety syringe includes an inner tubular body, plunger, and needle extending from a distal end of said inner tubular body, an outer tubular housing concentrically and slidingly surrounding at least a portion of the inner tubular body and biased apart from the inner tubular body. A recess is defined within an interior wall surface of the outer tubular housing, and a latch attached to a distal end of the inner tubular body. The latch includes a ring-shaped collar attached to the distal end of the inner tubular body and includes a cantilevered push-stop. A portion of the cantilevered push-stop is sized to fit within the recess when the latch is sufficiently disposed within the outer tubular housing.

11 Claims, 6 Drawing Sheets

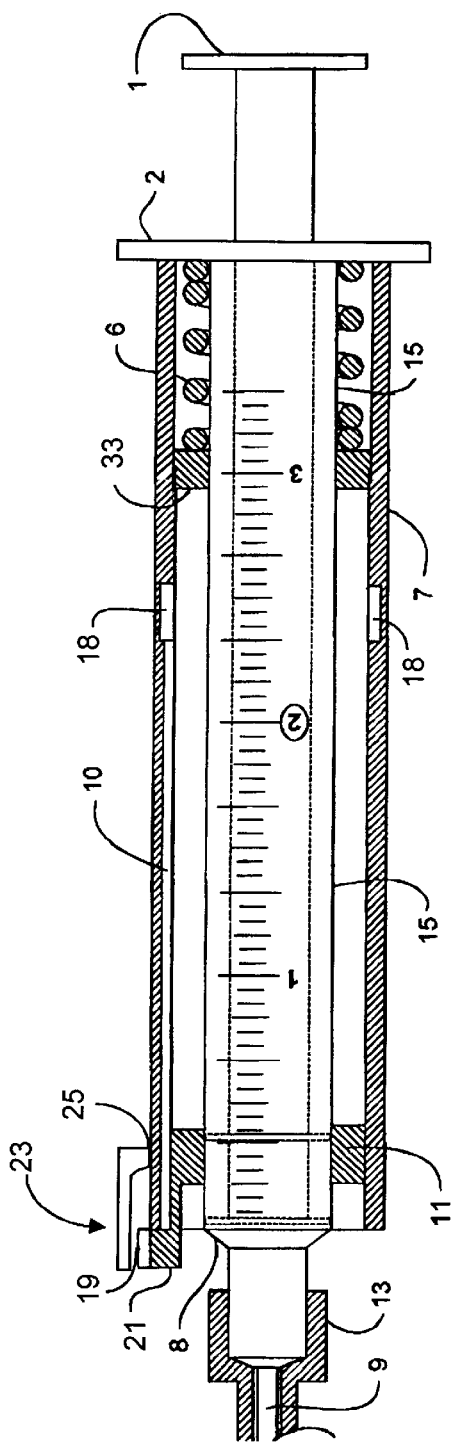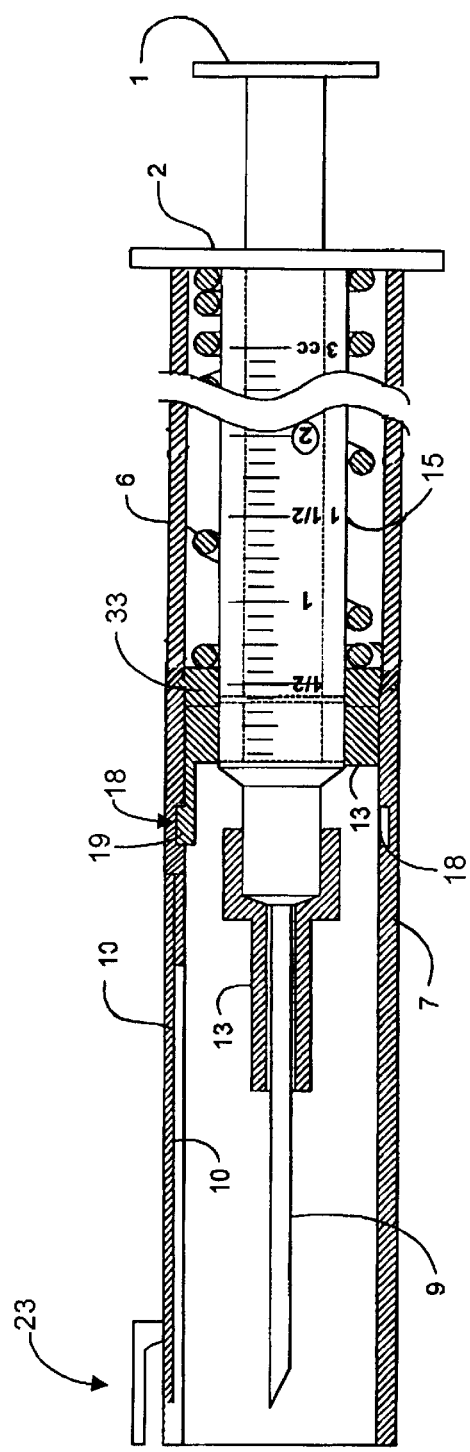

METHOD AND DEVICE TO PROTECT SYRINGES AND SIMILAR MEDICAL INSTRUMENTS

RELATIONSHIP TO PENDING APPLICATION

This is a continuation-in-part of applicant's co-pending U.S. patent application Ser. No. 09/524,144, filed Mar. 10, 2000 entitled "Safe Needle Device for Syringe", now U.S. Pat. No. 6,322,540 (issued Nov. 27, 2001), and a CIP of PCT/US01/07646 filed on Mar. 9, 2000, pending.

FIELD OF THE INVENTION

The present invention relates generally to sharp medical instruments such as syringes and needles, and more particularly to protecting users of such instruments from inadvertent injury from the instruments.

BACKGROUND OF THE INVENTION

Adequately protecting physicians, nurses, and other medical staff users of sharp medical instruments has always presented a challenge. More recently, with the spread of AIDS, hepatitis, and other highly infectious diseases, it has become even more important to protect users of syringes, scalpels, and other sharp devices from injury and infections, especially in a health care facility. The Needle Stick Safety and Prevention Act passed unanimously in both houses in 2000, and thirty-five states have enacted legislation mandating protection to medical staff at such facilities from wounds or other injury resulting from use of such instruments. See for example State of California Labor Code §144.7(d).

Various protective devices have been attempted in the prior art, but generally such devices have not functioned well, were not user-friendly, and generally have not been widely accepted, notwithstanding a need for such devices. Many prior art devices overlook the fact that when a medical practitioner uses such a device, a syringe for example, at best one hand is available to hold the device. For example, a nurse preparing a patient for an injection with a syringe requires one hand to clean the patient area to be injected, and one hand to hold the syringe while injecting the needle and syringe contents into the patient's tissue. Upon injecting the syringe contents, the nurse will withdraw the needle from the patient with one hand, and typically will press a compress against the injection site with the other hand, to halt any flow of blood.

In typical prior art protective devices, the nurse or other medical practitioner must now use the free hand to twist a cover over the syringe or sharp portion of other medical device. Thus, one hand is required to hold the device while the other hand twists the protective prior art cover. In the interim, the needle portion of the device may drip blood onto the patient or the nurse, with resultant contamination. Further, unless great care is exercised while maneuvering the syringe to utilize the protective prior art cover, the skin of the medical practitioner may inadvertently be punctured, again with potentially serial adverse medical consequences.

An exemplary prior art protective device is disclosed in U.S. Pat. No. 5,885,257 to Badger (1999), a somewhat cumbersome device in which a compressed spring retracts a needle syringe into a holdable barrel after use, and wherein a second hand appears required to actuate the spring release mechanism. Unfortunately, during an injection when Badger's spring is compressed, the needle may not extend sufficiently clear of the device to attain a proper injection depth. Further, Badger disclosed a notched plunger intended to be broken after use, to prevent reuse of the syringe. But if the plunger is not broken, the syringe is free to be reused, in violation of good medical practice and federal law. Further, the spring may urge the notched plunger so far rearward to allow blood or other fluid to escape from the rear end of the barrel.

Thus, there is a need for a protective device for a syringe or similar medical instrument that protects the instrument while allowing the instrument to be used with one hand. Such device should further prevent the instrument from being used after an initial use, and should adequately protect users from puncturing or otherwise wounding themselves with he instrument after it has been used. Finally, such device should prevent users against contamination from fluids within or in contact with the instrument.

The present invention provides such a device.

SUMMARY OF THE INVENTION

Applicant's parent application disclosed a one-time useable needle-stick safety syringe that could be used with one hand. The syringe included an inner tubular body (body) with an extended needle at one end, and a plunger mechanism at the other end. A larger diameter protective outer tubular housing (housing) concentrically surrounded at least a portion of the body, and included a washer-like plug at the syringe plunger end and a washer-like collar with a cantilevered push-stop at the syringe needle end. The body was free to slide axially within the housing. A spring surrounded the plunger near the syringe plunger end to urge the housing toward the syringe needle end. Before use, the push-stop prevented the spring from urging the housing over the syringe needle end. After use, the person using the syringe would press the push-stop with a finger of the hand hold the syringe. This action allowed the housing to be urged by the spring over the syringe needle end. A slot in the housing near the syringe piston end then captured the push-stop, thus preventing reuse of the syringe, since the needle region was now surrounded by the housing. In this configuration, the syringe was safe in that the needle was protected; a person would literally have to insert a finger into the housing before contacting the needle.

The present invention advantageously further prevents an attempt to reuse the syringe by replacing the slot in the housing with a recess in the inner housing surface. Preferably the recess defines an annular shape such that regardless of any twisting between the push-stop and the syringe housing, the recess will always engage a portion of the push-stop when the housing surrounds the push-stop. After one use of the present invention, as the housing is urged toward the syringe needle end, the recess traps the push-stop completely within the housing, to prevent reuse. With this configuration, one cannot readily release the push-stop, even in a very deliberate attempt to reuse the syringe. Preferably the present invention now includes a second outer trigger that actuates the push-stop to promote more consistent and ready retraction. In addition, the present invention preferably disposes the compression spring within, rather than without, the syringe. Finally, the ridge and groove feature of the parent invention may be dispensed with to minimize friction when using the present invention.

Other features and advantages of the invention will appear from the following description in which the preferred embodiments have been set forth in detail, in conjunction with the accompanying drawings.

BRIEF DESCRIPTION OF THE DRAWINGS

FIG. 6 is a cross-sectional view of a syringe in an unreleased disposition showing a recess in the syringe housing, according to the present invention;

FIG. 7 is a cross-sectional view is the syringe shown in FIG. 5, but in a released disposition in which the needle is protected by an outer tubular body that cannot readily be released for reuse of the syringe, according to the present invention.

DETAILED DESCRIPTION OF THE PREFERRED EMBODIMENTS

To provide a better understanding of the present invention, the invention of applicant's parent invention, now U.S. Pat. No. 6,322,540 (2001) will first be described with reference to FIGS. 1–4.

Figure 1:
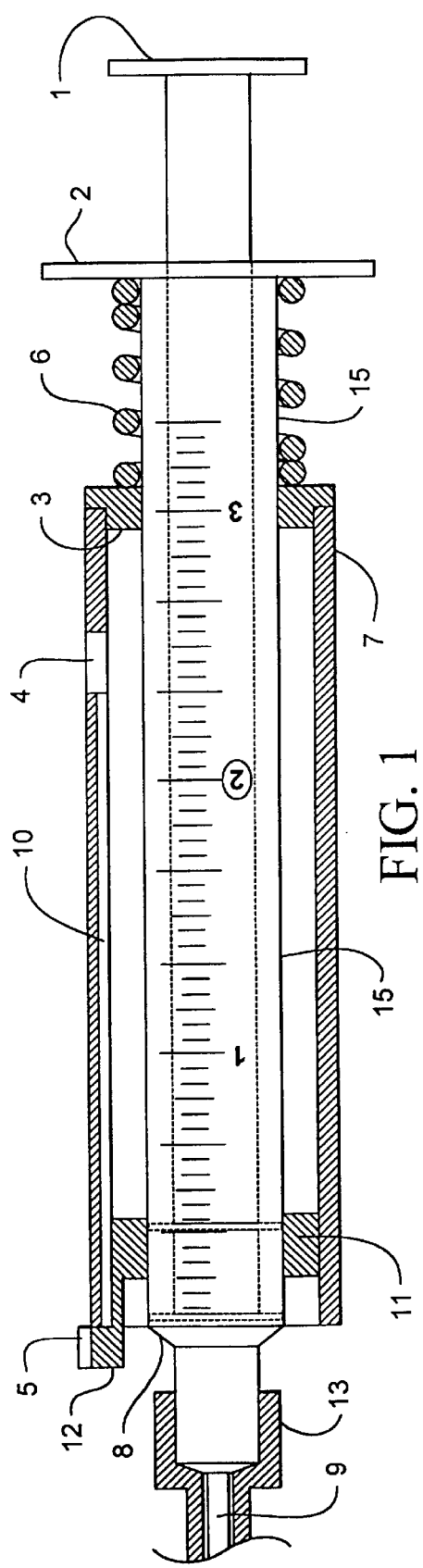
FIG. 1 is a cross-sectional view of a syringe in an unreleased disposition, according to an embodiment of applicant's parent application.

FIG. 1 depicts a typical commercial syringe of the so-called "TB" type, that is a syringe with a 3 cc capacity. The syringe shown operates in a standard fashion, and includes a plunger 1 that slides within an inner tubular body 15. Inner tubular body 15 includes a flange 2 at its proximal end, an extended needle 9 at its distal end 8, and further includes a protective cover 13.

Figure 4:
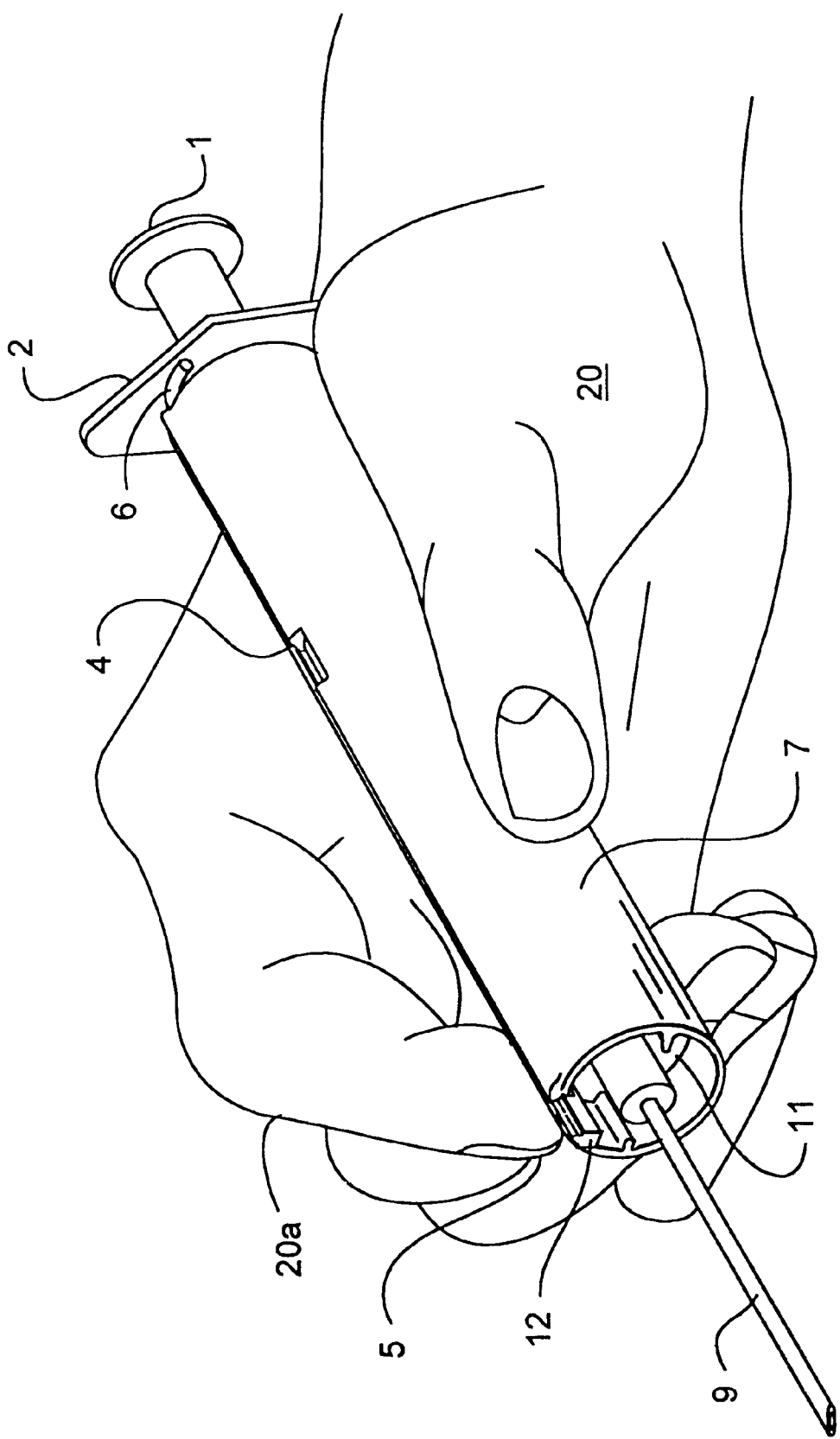
FIG. 4 is a perspective view showing use of the syringe of FIGS. 1–3 in use by medical personnel.

In accordance with applicant's parent invention, a collar 11 is provided at distal end 8, the collar being permanently or frictionally fitted or affixed onto the distal end of tube 15. Collar 11 includes a flexible cantilevered stop 12 that has a button-type termination 5 that is easily engageable by a human hand 20, as shown in FIG. 4.

As shown in FIG. 1, the syringe further includes a protective sleeve type tubular body 7 that includes a plug 3 at its distal end. Tubular body 7 has a larger diameter than inner syringe body 15, and can slide concentrically over the syringe body. Syringe body 15 is freely slidable within plug 3.

A coil spring 6 is initially slid on the inner tubular body 15 and abuts against the flange 2 at one spring end, with the other spring end being retained by abutment unit 3. In this unreleased state, cantilevered stop 12 retains spring 6 in a compressed condition with button 5 because cantilevered stop 12 hooks against the proximal edge of the tube 7.

In actual construction, spring 6 would be slid onto the syringe tube. Thereafter the plug 3 is slid against spring 6, and outer protective sleeve 7 is slid on, compressing spring 6 and mating with plug 3. Finally, collar 11 is permanently affixed, for example, by friction fitting or even glueing.

Figure 3:
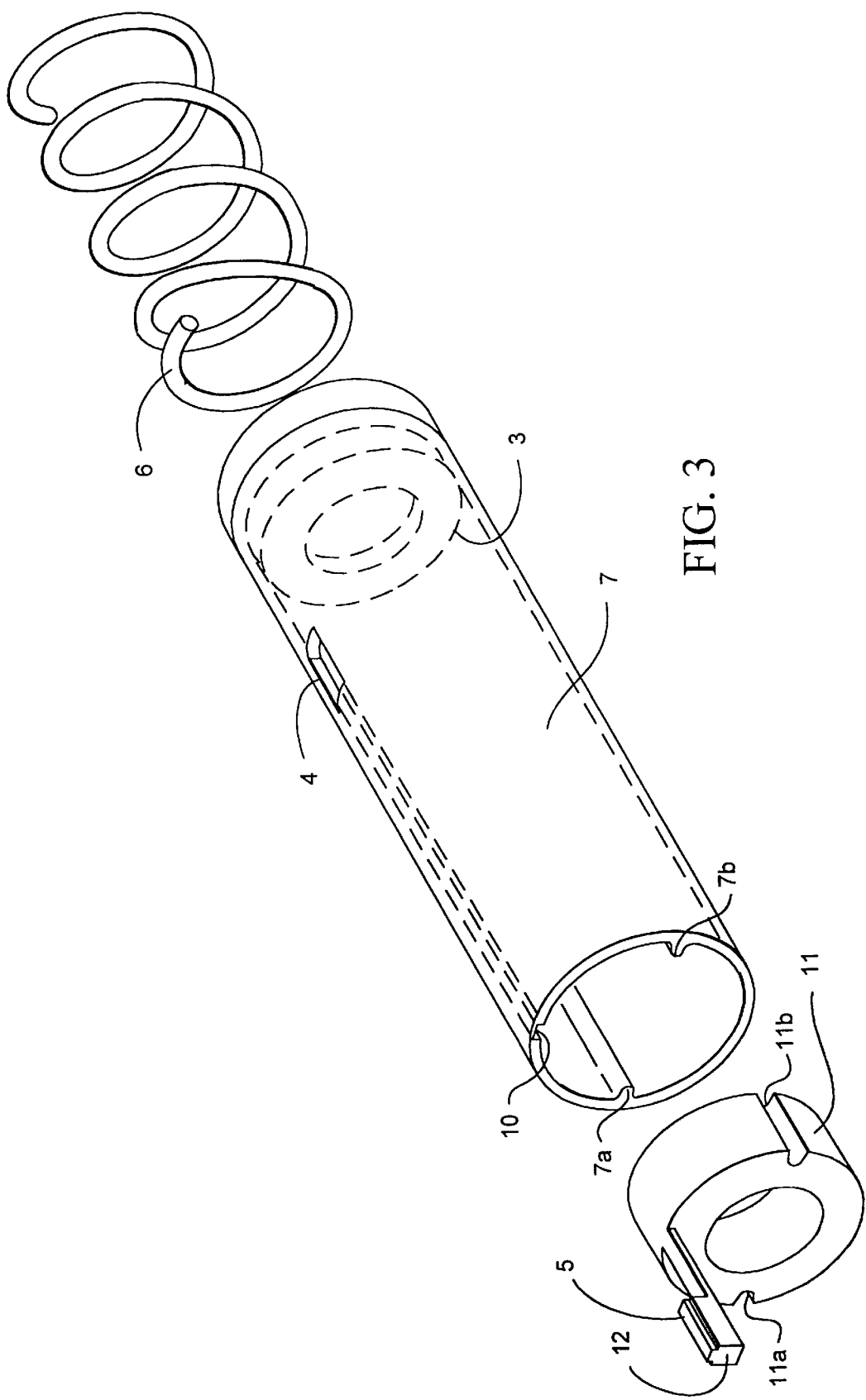
FIG. 3 is an exploded perspective view showing a portion of the syringe of FIGS. 1 and 2.

FIG. 3 depicts further details of applicant's parent invention, and depicts spring 6 and abutment 3, where outer protective tubular body 7 includes an interior groove 10. When it is depressed by a human finger, stop 12 is guided by groove 10 to slot 4 in the proximal end of tubular body 7. To further prevent twisting and enhance the travel of the collar 11, the collar includes a pair of diametrically opposed grooves 11a, 11b that mate with a similar pair of axial guides 7a and 7b on the interior of tubular body 7. As described above, the outer diameter of collar 11 is freely slidable within tubular body 7, however its inner diameter is frictionally fitted or permanently affixed to the inner tubular body of syringe 15.

Figure 2:
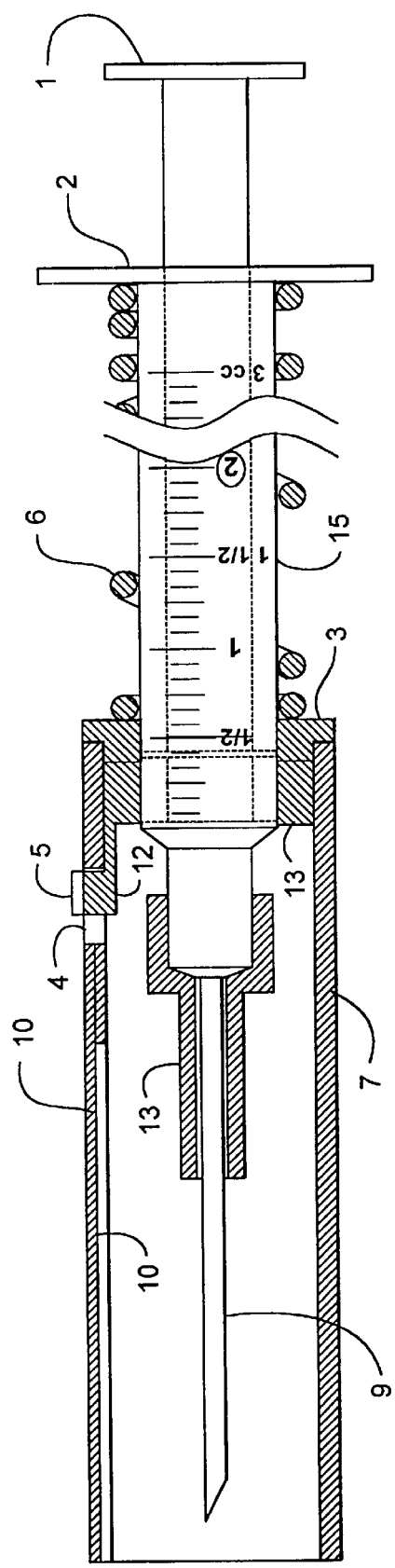
FIG. 2 is a cross-sectional view is the syringe shown in FIG. 1, but in a released disposition in which the needle is protected by an outer tubular body.

After a patient has been injected with the syringe, needle 9 is withdrawn as shown in FIG. 4, and held in one hand 20 by the nurse or other medical practitioner. The other hand, of course, can be used to press the area of injection. Then with a suitable finger such as the index finger 20a, button 5 on cantilever 12 is pressed. As shown in FIG. 2, this action releases tube 15 and allows the force of spring 6 to relatively move the outer protective tubular body to cover needle 9. As this occurs in channel 10, button 5 and its cantilevered end 12 move and are captured by slot 4.

As apparent from FIG. 2, this process is not readily reversible. There is no simple way to effectively depress button 5 to again expose needle 9, e.g., to attempt to reuse the syringe. Thus, the embodiment shown enhances safety of the administering medical practitioner, who can now dispose of the syringe. Protective cover 10 may be fabricated from a transparent material such as plastic or glass to enable viewing the syringe contents and the gradations, as shown in FIG. 1.

Thus, applicant's parent invention provided an improved needle stick safety 20 syringe that could be used with one hand. The syringe could be easily handled by unskilled persons, without special tools or skills or instructions. Further, outer protective body or sleeve 10 was constructed to preclude rotation or twisting in a retraction mode. As a result, a more linear alignment was achieved, as was straight retrieval of the needle into the sleeve, directly into the locking slot.

Figure 5:
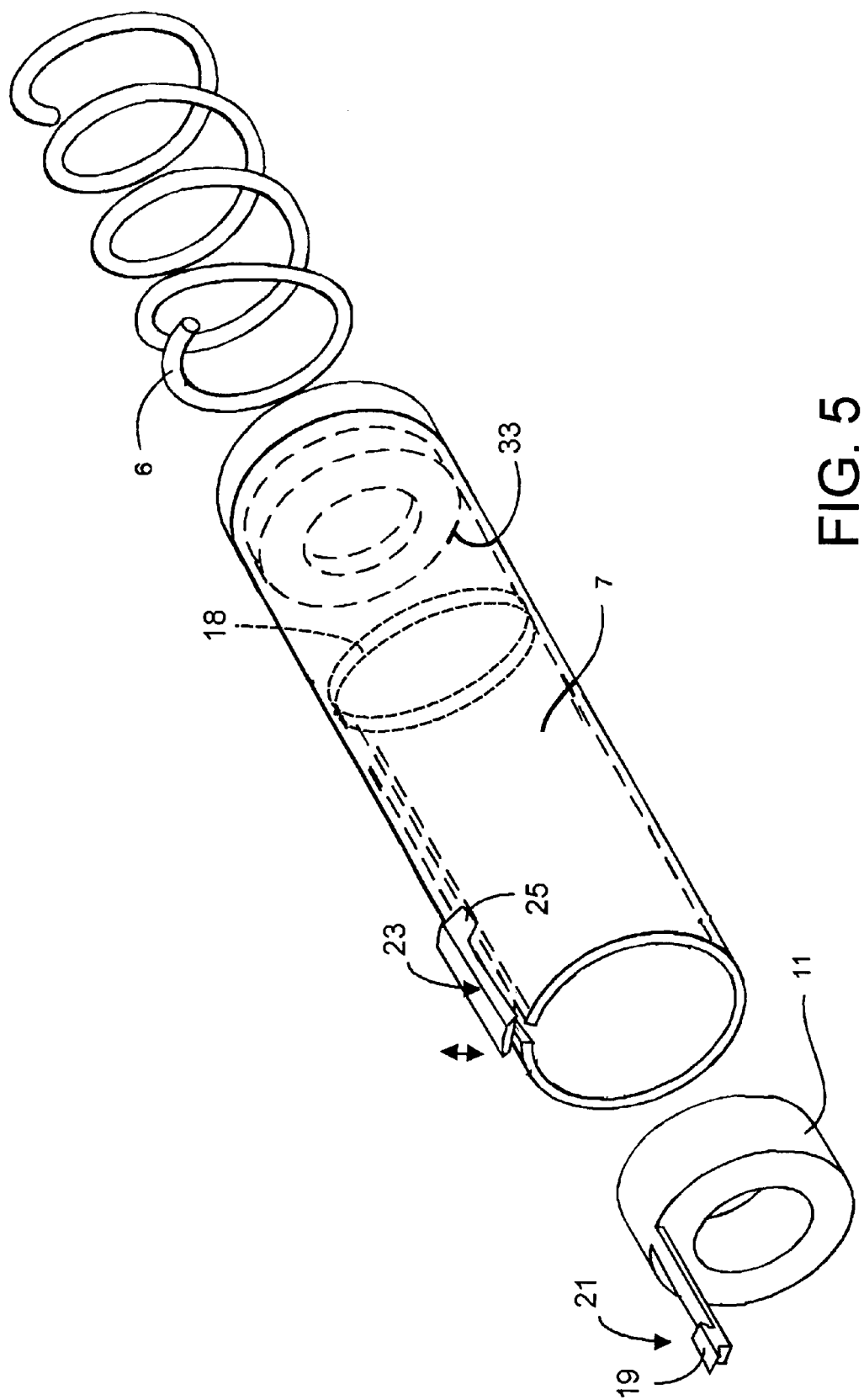
FIG. 5 is an exploded perspective view of a modified cantilever button and a syringe housing including an inaccessible recess, according to the present invention.

Turning now to FIG. 5, an embodiment of applicant's present invention is depicted. Comparing the present invention shown FIG. 5 with applicant's parent invention shown in FIG. 3, several changes are apparent. In the present invention a recess 18 is formed in the inner wall of housing 7 and is sized to engage and trap the upper surface 19 of a somewhat modified cantilever button or push-stop 21. To ensure that recess 18 will always trap a portion of surface 19 of push-stop 21, it is preferred that the recess be formed as an annulus within the housing interior wall. Thus, regardless of any rotation or twisting between the push-stop and the syringe housing, trapping action can still occur.

Preferably an external trigger 23 is mounted at end 25 to the exterior distal surface of housing 7. Further, the abutment 3 structure shown in FIGS. 1 and 2 regarding applicant's parent invention is preferably now a washer 33, and the length of barrel housing 7 is extended to enclose spring 6, as best seen in FIGS. 6 and 7.

As noted, the present invention optionally includes an exterior trigger 23 that is preferably fabricated from a resilient or at least slightly resilient inexpensive material, e.g., plastic, rubber, etc. and can operate in cantilever fashion. The cooperative action between interior push-top 21, exterior trigger 23 (if present) and interior recess 19 may further be appreciated from FIGS. 6–9. FIG. 6 shows the syringe, for example, just after use in injecting a patient.

Figure 8:
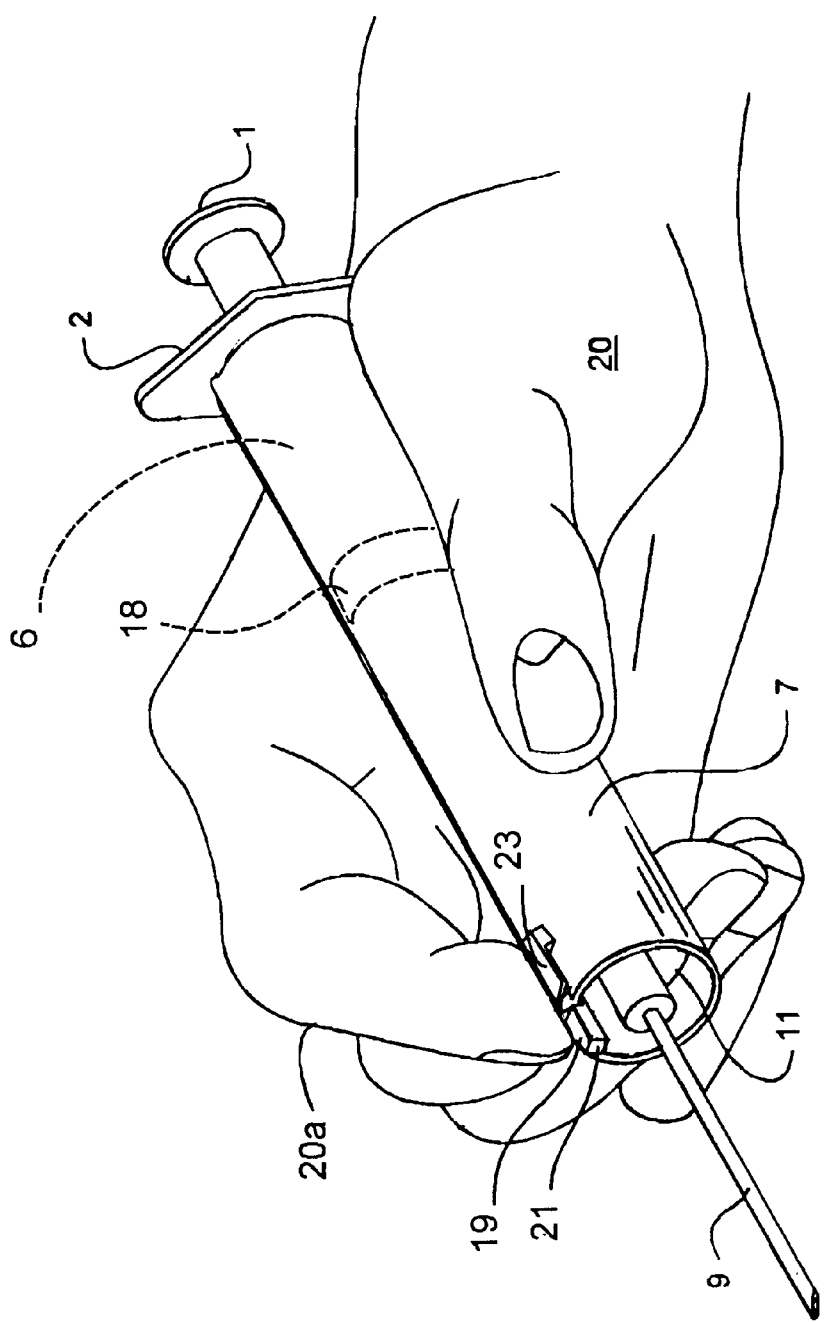
FIG. 8 is a perspective view showing use of the syringe of FIGS. 5–7 in use by a medical practitioner.

As shown in FIG. 8, as a user-practitioner presses down on the distal end of exterior trigger 23, e.g., with a forefinger of the hand holding the syringe, at least the distal portion of the exterior trigger is displaced downward to press against a portion of upper surface 19 of inner push-stop 21. Once the distal end of push-stop 21 is urged downward, e.g., by finger force upon exterior trigger 23, housing 7 is urged by spring 6 to move over collar 11 and in the direction of the needle (not shown, but to the left in FIGS. 5–8). As housing 7 moves to the left (in the orientation shown), recess 18 on the inner surface of housing 7 will trap upper portion 19 of interior push-top 21, as shown in FIG. 7. As noted, since recess 18 preferably defines an annulus, e.g., the recess is defined as a 360° groove in the inner wall of housing 7, trapping can always occur regardless of twisting or rotation of the push-stop.

Once such trapping occurs, one cannot readily free push-stop surface 19 from recess 18, which is to say, a user cannot readily re-use a syringe according to the present invention as the needle portion will remain surrounded by the distal portion of housing 7. By contrast, in applicant's parent invention a determined individual might force a narrow tool into window slot 4 that was formed through housing body 7 to try to depress cantilevered stop 5 downward, to free it from the through slot 4. If such effort was successful, housing 7 might then be slid away from the needle to (wrongfully) permit the syringe to be reused. But in the present invention, recess 18 is not accessible from outside of housing 7, e.g., it is merely a recess in the inner wall of the housing, and is not a through window slot as in the parent invention.

It will be appreciated that exterior trigger 23 could be dispensed with, if desired, and interior push-top 21 deflected downward by direct contact with an object, e.g., a user-practitioner's finger, to cause housing 7 to surround needle 9 (as shown in FIG. 7). However use of a so-called compound trigger comprising an inner push-top 21 and an external trigger 23 to promote a more consistent and easy retraction operation.

Note too from FIGS. 5 and 8 that axial guide ridges 7a, 7b and corresponding grooves 11a, 11b (which were shown in FIG. 3) are preferably dispensed with, to minimize friction when using the present invention. It will also be appreciated from FIGS. 6–8 that in the present invention, bias spring 6 preferably is disposed within barrel housing 7, rather than external to the housing as was shown in FIGS. 1 and 2 for applicant's parent invention. Preferably the length of barrel housing 7 is extended somewhat over that used in the parent invention, to ensure adequate coverage of spring 6 and needle 9 before and after retraction, respectively.

Modifications and variations may be made to the disclosed embodiments without departing from the subject and spirit of the invention as defined by the following claims.

What is claimed is:

1. A needle-stick safety syringe, comprising:
    an inner tubular body, plunger, and needle extending from a distal end of said inner tubular body;
    an outer tubular housing concentric with and sized to fit around at least a portion of said inner tubular body and to slide freely thereon;
    a spring disposed to bias apart said inner tubular body and said outer tubular housing;
    a recess defined within an interior wall surface of said outer tubular housing; and
    a latch attached to a distal end of said inner tubular body, said latch including a ring-shaped collar permanently attached to said distal end of said inner tubular body and having an outer diameter sized to slide freely within said outer tubular housing and further including a cantilevered push-stop, said cantilevered push-stop including a portion sized to fit within said recess when said latch is sufficiently disposed within said outer tubular housing, said latch push-stop engaging against a distal edge of said outer tubular housing to oppose bias of said spring;
    wherein when said cantilevered push-stop is urged away from said outer tubular housing, said spring biases said outer tubular housing over said latch and said recess engages a portion of said push-stop.

2. The syringe of claim 1, wherein said recess defines an annular shape within said interior wall surface of said outer tubular housing.

3. The syringe of claim 1, wherein said recess is disposed adjacent a proximal end of said outer tubular housing.

4. The syringe of claim 1, further including an exterior trigger disposed on an outer surface of said outer tubular housing adjacent a distal end thereof;
    wherein user-exerted force on said exterior trigger urges said cantilevered push-stop away from said outer tubular housing.

5. The syringe of claim 4, wherein said exterior trigger is a cantilever trigger.

6. The syringe of claim 4, wherein said exterior trigger is selected from a material group consisting of (a) rubber, (b) plastic, and (c) flexible metal.

7. The syringe of claim 1, wherein said spring is disposed within said outer tubular housing.

8. A needle-stick safety syringe, comprising:
    an inner tubular body, plunger, and needle extending from a distal end of said inner tubular body;
    an outer tubular housing concentric with and sized to fit around at least a portion of said inner tubular body and to slide freely thereon;
    a spring disposed within said outer tubular housing to bias apart said inner tubular body and said outer tubular housing;
    a recess defining an annulus within an interior wall surface of said outer tubular housing adjacent a proximal end of said outer tubular housing; and
    a latch attached to a distal end of said inner tubular body, said latch including a ring-shaped collar permanently attached to said distal end of said inner tubular body and having an outer diameter sized to slide freely within said outer tubular housing and further including a cantilevered push-stop, said cantilevered push-stop including a portion sized to fit within said recess when said latch is sufficiently disposed within said outer tubular housing, said latch push-stop engaging against a distal edge of said outer tubular housing to oppose bias of said spring;
    wherein when said cantilevered push-stop is urged away from said outer tubular housing, said spring biases said outer tubular housing over said latch and said recess engages a portion of said push-stop.

9. The syringe of claim 8, further including an exterior trigger disposed on an outer surface of said outer tubular housing adjacent a distal end thereof;
    wherein user-exerted force on said exterior trigger urges said cantilevered push-stop away from said outer tubular housing.

10. The syringe of claim 9, wherein said exterior trigger is a cantilever trigger.

11. The syringe of claim 9, wherein said exterior trigger is selected from a material group consisting of (a) rubber, (b) plastic, and (c) flexible metal.

* * * * *